US005732122A

United States Patent [19]

Tibbals

[11] Patent Number: 5,732,122
[45] Date of Patent: Mar. 24, 1998

[54] X-RAY MARKER APPARATUS AND METHOD

[75] Inventor: Harry Fred Tibbals, McKinney, Tex.

[73] Assignee: Eastman Kodak Company, Rochester, N.Y.

[21] Appl. No.: 733,379

[22] Filed: Oct. 17, 1996

[51] Int. Cl.[6] .................................................. H05G 1/28
[52] U.S. Cl. ............................................ 378/162; 378/165
[58] Field of Search ................................... 378/162–165

[56] References Cited

U.S. PATENT DOCUMENTS

| | | |
|---|---|---|
| 3,518,428 | 6/1970 | Ring . |
| 3,619,611 | 11/1971 | Hall . |
| 5,388,581 | 2/1995 | Bauer et al. ............................. 378/162 |

*Primary Examiner*—Craig E. Church
*Attorney, Agent, or Firm*—Susan L. Parulski

[57] ABSTRACT

A marker apparatus and method for identifying radiation imaging recording media, particularly x-ray media. The apparatus includes a container having a recessed area and a reservoir communicable with the recessed area. A surface, disposed within the recessed area, includes a marking area on which identifying characters are formed using a marking instrument. An imaging media comprised of a material opaque to radiation is disposed within the reservoir. Flow of the imaging media is effected from the reservoir into the recessed area and across the surface to collect at the identifying characters. In one embodiment, the surface is a deformable surface on which depressions are formed, and the imaging media collects in the depressions. In another embodiment, the surface is a magnetic surface which attracts magnetically-attractable imaging media.

26 Claims, 5 Drawing Sheets

X-RAY MARKER APPARATUS AND METHOD

FIELD OF THE INVENTION

The apparatus relates to radiation imaging techniques, and more particularly, to an apparatus and method for providing identification on exposed x-ray media used for radiation imaging.

BACKGROUND OF THE INVENTION

Radiation imaging techniques include positron emission tomography, nuclear magnetic resonance (NMR), nuclear medicine, and x-ray imaging. In the production of x-rays, an x-ray technician normally employs an identifying marker, cassette, or nameplate during the exposure of radiation to the subject matter. Such a marker provides a positive means of identifying subject matter on each x-ray image. For example, in a situation wherein a foot is to be x-rayed, it is desirable to provide an identification marker which may be positioned within the scope of the x-ray during exposure to identify that foot which is being x-rayed. The subject matter may include, for example, the patient's name, the item being x-rayed, or insurance information.

Current techniques of providing such a marker include a flat plastic plate on which movable type comprised of solid lead letters is secured, for example by adhesive, to form a word or words to identify that portion of the body being x-rayed or the patient's name. Identification of the particular x-ray is immediately determined by reading the characters which the solid letters form. Alternatively, lead letters can include a bonded layer of magnetic metal, allowing the lead letters to be temporarily attached to a magnetic plate to form a word or words. In a further alternative, strips of lead or lead paste are joined together and secured, for example by adhesive, to a flat plate to form letters, which in turn form words. These strips of lead or lead paste would be securely affixed to the flat plate and used repeatedly to form the same words on many x-ray images. An example of such words may be the name of the hospital or anatomical terms.

With the techniques employing movable type, the technician handles the strips of lead or lead letters. Because they are handled, they are subject to loss, damage, and wear from ordinary use. Further, manual handling is time consuming and prone to errors. In addition, special coatings may be required to reduce the potential health hazards from handling lead materials.

U.S. Pat. No. 3,518,428 (Ring) relates to a magnetically attractive identifying plate for attachment to x-ray film cassettes. Words are formed by making depressions by pressing letter templates into a magnetized sheet. The depressions are then filled with a fine lead powder paste. The surface of the magnetized sheet is covered to seal the powdered lead material. With such an apparatus, the identifying plate, once made, is not easily alterable, and the lead paste is not readily re-usable. Since the depth and size of the letter templates are predetermined, each identifying plate is suitable for use with a narrow range of x-ray exposures and image sizes. Typically, a multitude of identifying plates with the same words, but with varying thickness and letter sizes, are required to meet the labeling needs of an x-ray laboratory.

U.S. Pat. No. 3,619,611 (Hall) relates to an x-ray film marker wherein recesses are made in a body to form identifying characters. A metallic material opaque to radiation is forced into the recesses and allowed to harden. A cover plate is placed over the recesses. With such an apparatus, the marker, once made, is not easily alterable, and the metallic material is not readily re-usable. Further, multiple markers are needed to provide for different thickness and size of the identifying characters to compensate for different scales and levels of x-ray exposure and to obtain a legible label for each exposure level.

Accordingly, a need continues to exist for a robust x-ray marker wherein identifying characters can be formed within a short time frame. In addition, the components of the marker should be reusable, particularly the x-ray opaque material and the material on which the words are formed. Still further, the material on which the words are formed should be alterable, with the x-ray marker not being prone to damage during ordinary use. Preferably, lead material is isolated from being handled.

SUMMARY OF THE INVENTION

An object of the invention is to provide a robust x-ray marker wherein identifying characters can be formed within a short time frame.

Another object of the invention is to provide such an x-ray marker wherein the x-ray opaque material and the material on which the words are formed are reusable.

Still another object of the invention is to provide such an x-ray marker which is not prone to damage during ordinary use.

Yet a further object of the invention is to provide such an x-ray marker wherein any lead material is isolated from handling.

These objects are given only by way of illustrative example. Thus, other desirable objectives and advantages inherently achieved by the disclosed invention may occur or become apparent to those skilled in the art. The invention is defined by the appended claims.

According to one aspect of the invention, there is provided an apparatus for identifying radiation imaging recording media, particularly x-ray radiation. The apparatus includes a container having a recessed area and a reservoir communicable with the recessed area. A surface, disposed within the recessed area, includes a marking area on which identifying characters are formed using a marking instrument. Both the container and the surface are transparent to radiation. Disposed within the reservoir is an imaging media comprised of a plurality of generally spherical particles which are opaque to radiation. The imaging media is adapted to flow from the reservoir into the recessed area and across the surface whereby a portion of the particles collect at the identifying characters. In one embodiment, the surface is a deformable surface on which depressions are formed, and the imaging media collects within the depressions. In a second embodiment, the surface is a magnetic surface which can be magnetized by a magnetic field, and the magnetized areas attract magnetically-attractable imaging media.

According to another aspect of the present invention, there is provided a method for producing a marker for identifying radiation imaging recording media. The method includes forming identifying characters on a marking area of a container; effecting flow of an imaging media disposed within a reservoir of the container across the marking area; collecting a portion of the imaging media at the identifying characters; and effecting flow of the imaging media not collected at the identifying characters back to the reservoir. In one embodiment, the identifying characters are formed by forming depressions in a deformable surface. In a second embodiment, a magnetic field is applied to a magnetic surface of a container to form magnetized areas on the magnetic surface; the magnetized areas cooperating to form identifying characters. A portion of the imaging media collects at the magnetized areas.

The present invention provides a robust x-ray marker wherein identifying characters can be formed within a short time frame. The components of the x-ray marker are reusable, including the x-ray opaque material and the material on which the words are formed. Further, the opaque material is isolated from handling. The material on which the words are formed is alterable, and the x-ray marker is not prone to damage during ordinary use. The depth and width of the characters formed, and the overall size of the resulting words, can be readily varied to accommodate different image scales and different intensities of x-ray exposure to provide legible information under various conditions. The present invention is suitable for providing a range of imaging materials of varying degrees of opacity in interchangeable depressions.

BRIEF DESCRIPTION OF THE DRAWING

The foregoing and other objects, features, and advantages of the invention will be apparent from the following more particular description of the preferred embodiments of the invention, as illustrated in the accompanying drawings.

DETAILED DESCRIPTION OF THE INVENTION

The following is a detailed description of the preferred embodiments of the invention, reference being made to the drawings in which the same reference numerals identify the same elements of structure in each of the several figures.

Figure 1:
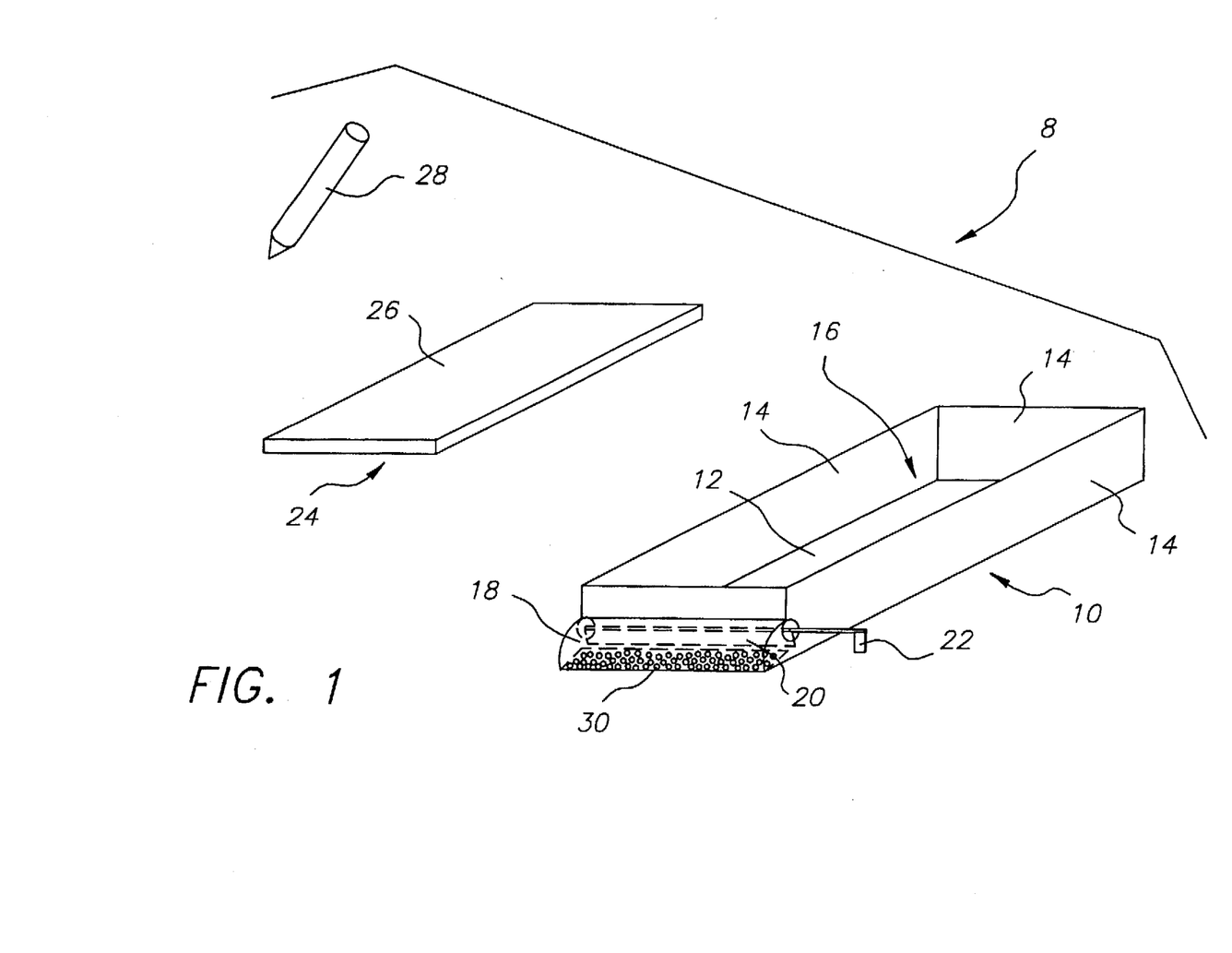
FIG. 1 shows a perspective view of an x-ray marker apparatus according to a first embodiment of the present invention.

FIG. 1 illustrates a first embodiment of an x-ray marker 8 in accordance with the present invention. X-ray marker 8 includes a container 10 having a bottom wall 12 and a plurality of side walls 14 to define a recessed area 16. Container 10 also includes a reservoir 18 capable of communication with recessed area 16. As illustrated in FIG. 1, reservoir 18 is positioned along one side wall of container 10. Alternately, reservoir 18 can be located along the perimeter of recessed area 16, or reservoir 18 and recessed area 16 may be combined as one area. Other configurations for reservoir 18 will be known to those skilled in the art. Container 10 is comprised of a material transparent to x-ray radiation.

An optional partition 20 is provided to control communication of reservoir 18 with recessed area 16. Partition 20, positioned intermediate recessed area 16 and reservoir 18, may include a door, gate, hinged cover, septum, or lid. A handle or lever 22 may be provided to control movement of partition 20 from outside container 10 to move (for example, by rotation) partition 20 between a first or open position, wherein recessed area 16 and reservoir 18 are in communication, and a second or closed position, wherein recessed area 16 and reservoir 18 are not in communication.

Figure 2:
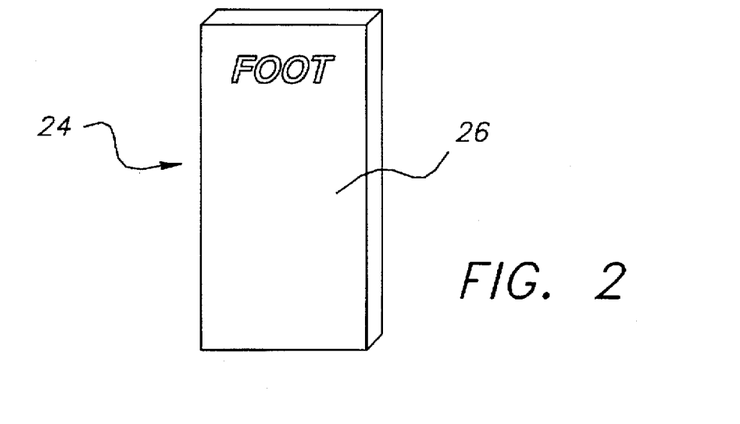
FIG. 2 shows a top view of a sheet having depressions.

A sheet 24 is configured to be positioned within container 10 on bottom wall 12, and preferably is of a shape and dimension substantially equal to recessed area 16. Sheet 24 is comprised of a material transparent to x-ray radiation, and includes a deformable surface 26. For example, surface 26 may be comprised of foam plastic, soft plastic, soft metal, low density paper product, or shape memory material. Surface 26 must be sufficiently deformable to enable a technician to form depressions or indentations in the surface which remain. These depressions can be formed by pressing or embossing using, for example, a writing instrument 28 such as a mechanical stylus or a pen. The depressions cooperate to form identifying characters. For example, FIG. 2 illustrates depressions in surface 26 forming the word "Foot".

Sheet 24 is removably mounted within recessed area 16 by conventional means, such as by fasteners or adhesive. The depressions can be formed in the surface prior to mounting sheet 24 within container 10, or after sheet 24 is mounted within container 10.

Referring again to FIG. 1, disposed within reservoir 18 is an imaging media 30 which is opaque to x-ray radiation, for example, a lead or bismuth based particulate preparation. Imaging media 30 is comprised of a plurality of generally spherical particles which can be in liquid or powder form. Preferably the particles are round and smooth to aid in the quasi-fluid movement of the particles.

In operation, if partition 20 is employed, partition 20 is initially disposed in its closed position to collect and secure imaging media within reservoir 18. Identifying characters are formed in the sheet 24, and sheet 24 is positioned within container 10. Lever 22 is moved to position partition 20 to its open position, and flow of imaging media 30 from reservoir 18 across surface 26 is effected. Flow can be effected, for example, by manipulating container 10 such as by tapping or shaking the container or rocking the container back and forth in a slightly elevated vertical position. Other means known to those skilled in the art may be employed to effect flow, such as blowing of the imaging media. By causing the flow of imaging media 30 over surface 26, a portion of imaging media 30 collects within the depressions formed on the surface; the depressions being sufficiently deep to maintain the imaging media within the depressions. Flow of the imaging media not collected in the depressions may be effected by further manipulating container 10 to return the non-collected imaging media to reservoir 18. Partition 20 may then be positioned to its closed position to secure the non-collected imaging media in reservoir 18. The depressions capture and temporarily hold imaging media 30 to allow the formation of an x-ray opaque image; imaging media 30 being held within the depressions by gravity when sheet 24 is positioned horizontally relative to ground.

The particles of imaging media 30 are sized such that they can collect within the depressions formed on surface 26. If too large for the depressions, the particles will not collect within the depressions. Suitable particle size allows sufficient particles to fill the depressions to provide a sharp image on an exposed x-ray.

For optimal filling and image sharpness, the diameter of the particles of imaging media 30 are prepared so as to be small relative to the width of the depressions formed on surface 26. Preferably, the diameter of the particles 30 are approximately 1/20th of the width of the depressions. For example, if the width of the depression is of about 0.2 inches, the diameter of the particles of imaging media 30 would preferably be about 0.01 inches. Such a sized particle may be a coarse spherical particulate powder, which, when comprised of a heavy metal such as lead, provide suitable flow characteristics when agitated. Flow characteristics may be increased with a suitable overcoating of the heavy metal without adversely affecting a desired opacity. Suitable particles for the present invention have a diameter sized from about 0.005 inches to about 0.2 inches; size is dependent on the size and desired sharpness of the formed word(s).

The desired depth of the depressions in surface 26 is dependent on the degree of x-ray opacity of imaging media 30 and the intensity of the x-ray beam of the x-ray equipment being utilized. For example, for high dosage x-ray intensity, imaging media 30 consisting of lead material collected in a depression up to about 0.1 inches in depth provides a suitable resulting image. Alternatively, a deeper depression may be used with an imaging media which is less opaque, such as steel beads, to produce a similar resulting image. For low dosage x-ray intensity, image media 30 comprised of lead material or bismuth particles provide a suitable resulting image if collected in a depression up to about 0.1 inches to about 0.3 inches formed in surface 26 of highly x-ray transparent sheet, such as plastic. Such depths are readily made with writing instrument 28, thereby providing the technician with convenient writing control.

Image sharpness is dependent on the degree of x-ray absorption, contrasting to scattering, produced by the material in the imaging media. To optimize free flow of the imaging media particles, the individual mass of the imaging media particles should be sufficient for a combination of gravity and inertial forces to free the imaging media particles from attraction to sidewalls 14, sheet 24, and each other.

An example of a suitable imaging media 30 is a powder comprised of spherical bismuth or lead beads having a diameter of approximately 0.015 inches and coated with a hard overcoat, for example, a copper plated layer of approximately 0.1 mm thickness. The overcoat is preferably compatible with container 10 and surface 26 to promote free flow and the reduction of static. The overcoat hardens the beads, preserves their spherical shape, provides a self-lubricating surface, and reduces the physical attraction of the beads to each other. Thus, a preferred implementation includes either a fine gauge bismuth shot or a coarse powder comprised of bismuth (or copper-coated lead) collecting in a surface made of Styrofoam mounted in a cardboard or plastic container. Other alternative materials for imaging media 30 include silver, gold, or other dense malleable metal.

With imaging media 30 collected within the depressions, the x-ray marker is ready for exposure by x-ray radiation. Since container 10 and sheet 24 are transparent to x-ray radiation, but imaging media 30 is opaque to x-ray radiation, the characters formed by the collected imaging media will be viewed within the exposed x-ray.

When the exposure to x-ray radiation is complete, handle 22 of partition 20 can be rotated to position partition 20 in its open position. Container 10 can again be manipulated to effect flow of the imaging media collected within the depressions to return and secure imaging media 30 to reservoir 18. Once imaging media 30 is returned to reservoir 18, hinge 22 is rotated to position partition 20 to its closed position. Thus, the image is "erased" when gravity aided by movement releases imaging media 30 from the depressions. Since the imaging media is not permanently affixed to sheet 24, the imaging material can be reused. Further, the user does not handle the imaging media.

If additional information is required in the image, further depressions can be formed in surface 26. If new information is required, sheet 24 can be removed from recessed area 16, and a new sheet 24 inserted. If surface 26 is comprised of a material which can be returned to its original planar shape, then surface 26 could be reused, thereby eliminating the need for additional sheets 24. For example, sheet 24 which is reusable may be comprised of a plastic or wood base coated with a layer of wax or soft polymer in which the depressions are formed. Such a sheet could be reused by re-coating the base with a new soft layer or by heating the sheet to re-flow the soft layer, causing the layer to fill the depressions. Alteratively, sheet 24 may be comprised of a thin, deformable metal to which a roller can be applied to remove the depressions. Further, sheet 24 may be comprised of a plastic material which, when the sheet is subjected to tension, resumes a flat surface.

Figure 3:
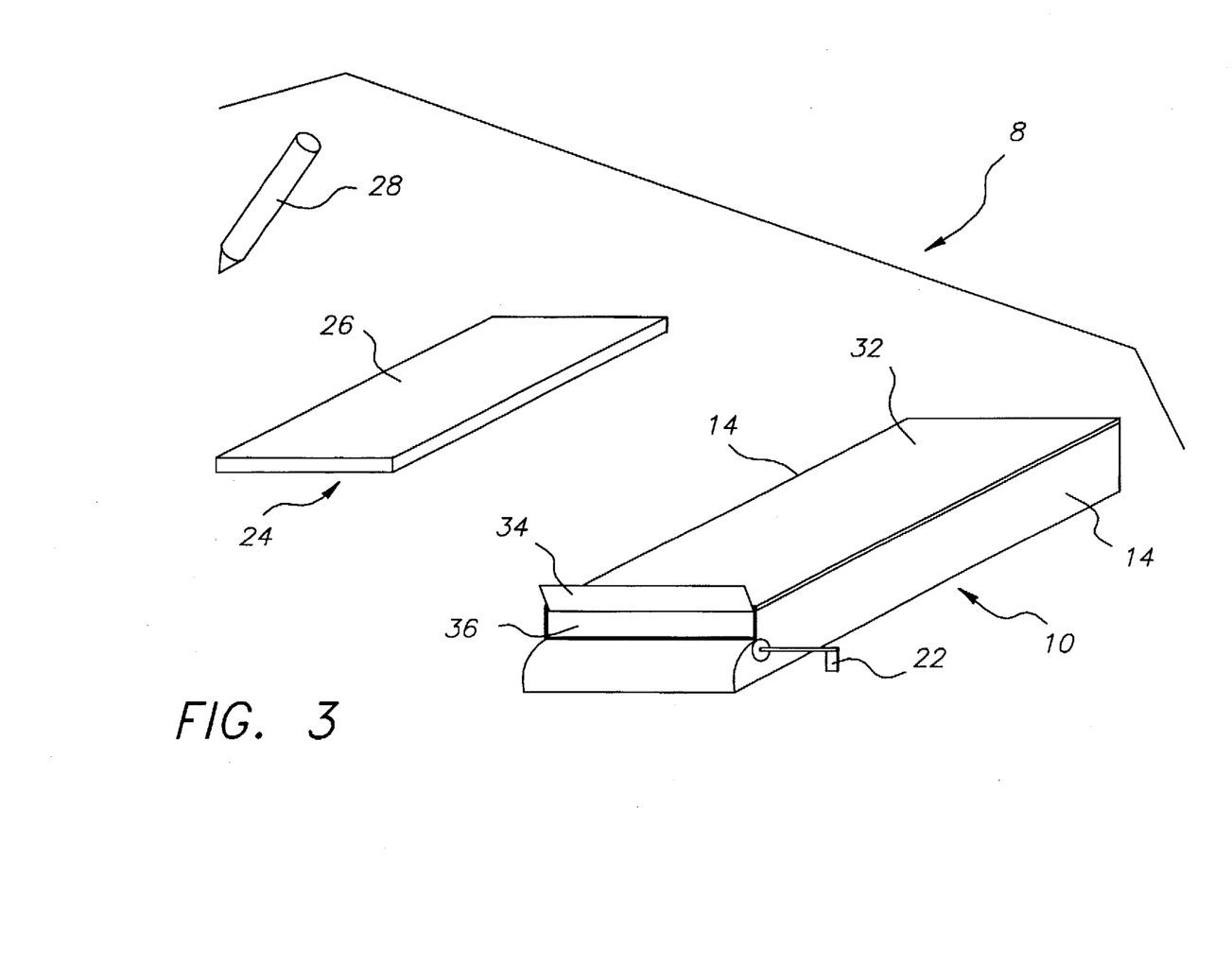
FIG. 3 shows the x-ray marker apparatus according to FIG. 1 having a cover.

As illustrated in FIG. 3, an optional cover 32 may be employed so as to enclose recessed area 16, resulting in container 10 being a sealed unit. Cover 32 would include a door or latch 34 movable between an open and closed position to define an opening 36 in container 10 through which sheet 24 can be inserted into container 10 and removed from container 10.

Figure 4:
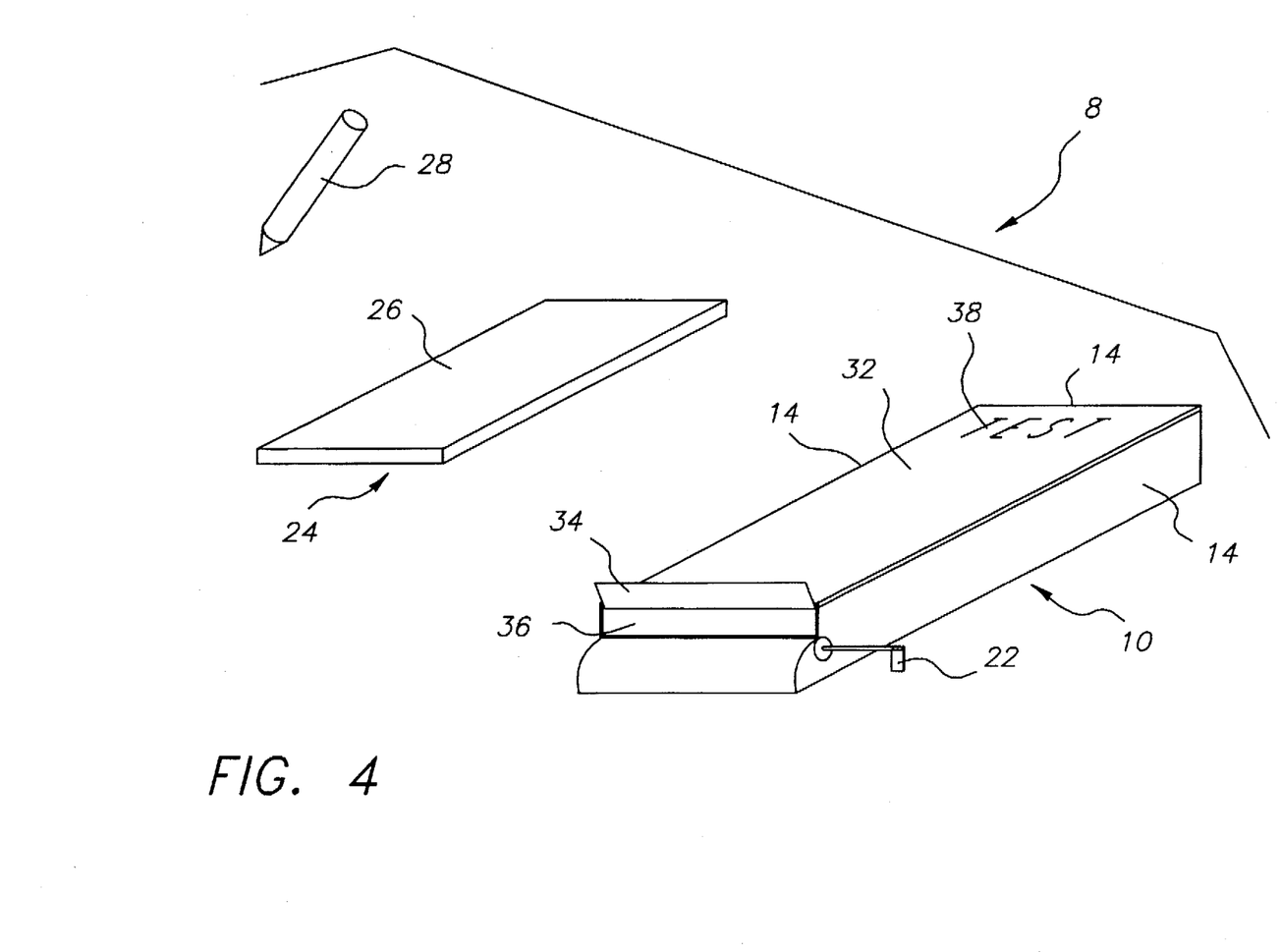
FIG. 4 shows the x-ray marker apparatus according to FIG. 3 having an informational area.

Further, cover 32 may include an informational area 38, as illustrated in FIG. 4, wherein an embedded or permanent pattern is positioned. Such a pattern could form a test pattern for the x-ray imaging equipment, or optionally, reflect a trademark, logo, or other pattern. Informational area 38 would be positioned on cover 32 so as to not overlap or interfere with the information positioned on sheet 24 once inserted in container 10.

Figure 5:
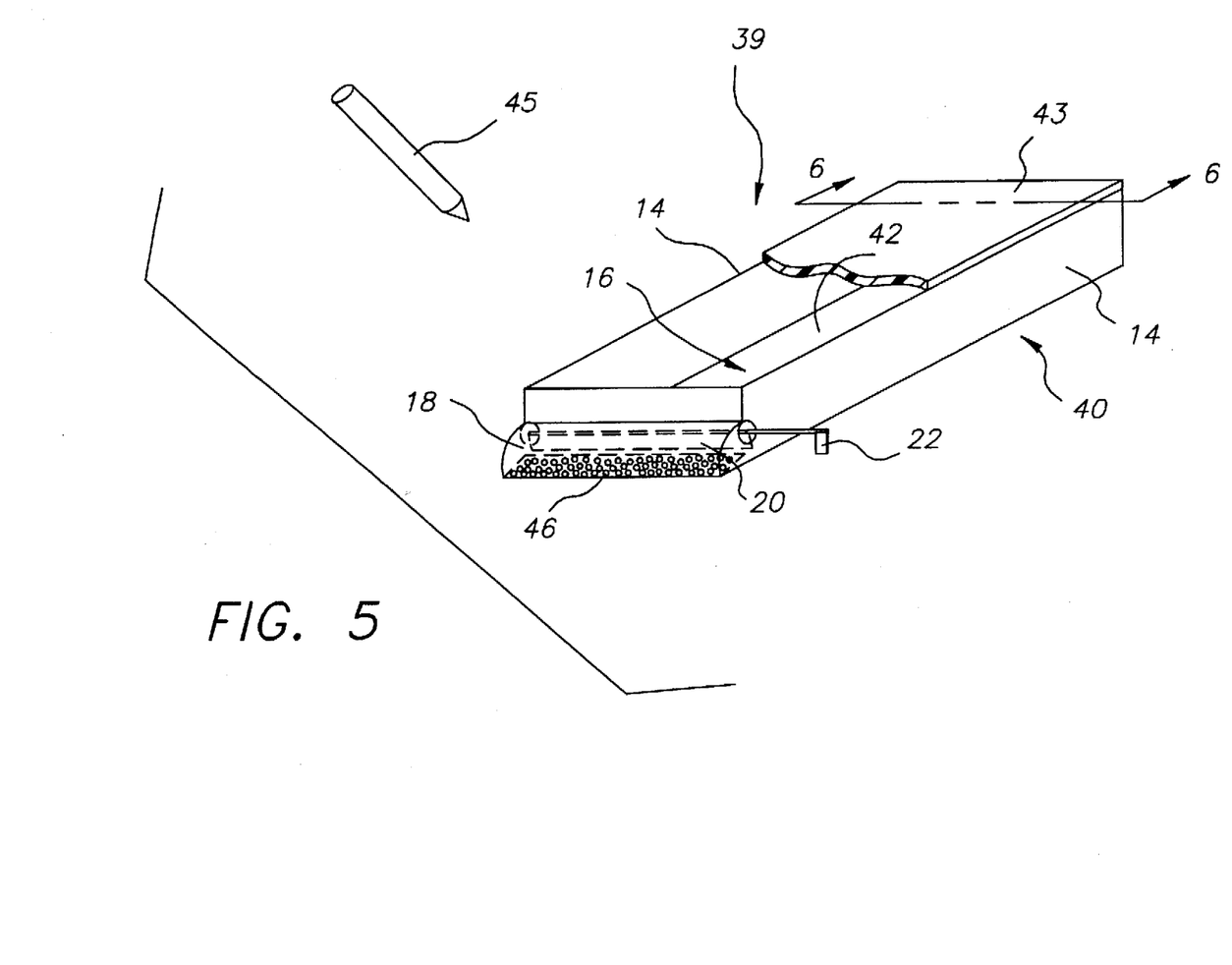
FIG. 5 shows a perspective view of an x-ray marker apparatus according to a second embodiment of the present invention.

A second embodiment of an x-ray marker, illustrated in FIG. 5, includes an enclosed container 40 defined by side walls 14, a bottom wall 42, and a top wall 43. The side walls, and bottom wall define recessed area 16. Reservoir 18 is positioned so as to be communicable with recessed area 16. An imaging media 46 is disposed within reservoir 18. Optional partition 20 having handle 22 is positioned to separate recessed area 16 and reservoir 18.

Figure 6A:
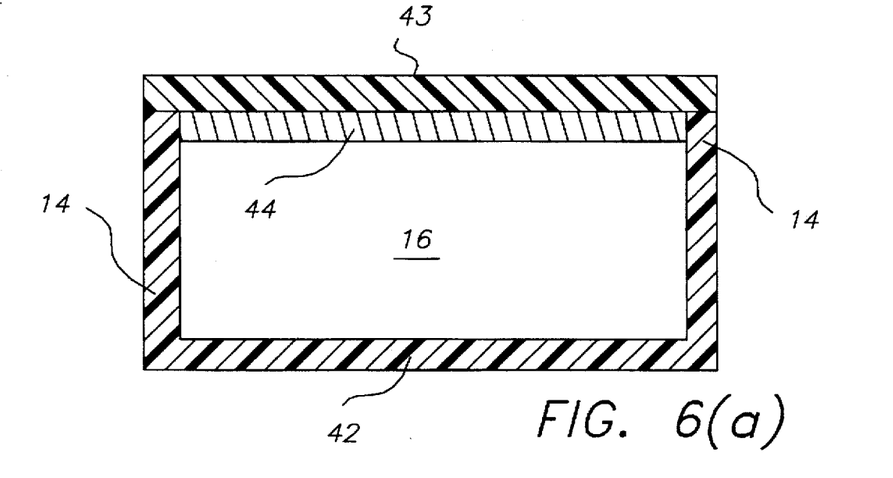
FIGS. 6(a) and 6(b) show alternative sectional views taken along line 6—6 of FIG. 5.
Figure 6B:
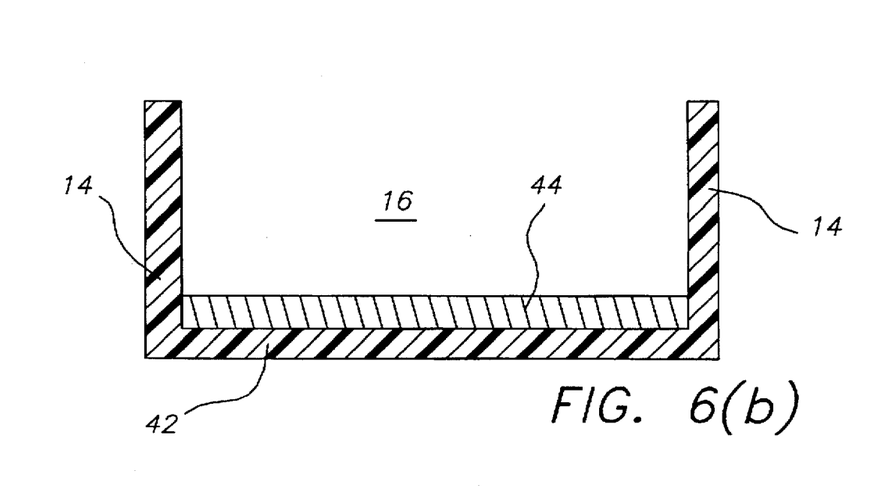

Referring to FIG. 6(a), top wall 43 includes a magnetic layer 44 which can be a coating on the surface of top wall 43, or alternatively, embedded within top wall 43. Optionally, as illustrated in FIG. 6(b), magnetic layer 44 may be coated or embedded in bottom wall 42. Layer 44 is comprised of a magnetizable material which can be rendered in a fixed magnetic state in localized areas by the application of a non-random externally applied magnetic field of suitable strength. Preferably, the magnetic state is temporary to allow re-use of the container, particularly layer 44 and the imaging media. Such materials include iron oxide, chromium oxide, iron, or other transition metals. The magnetic state of layer 44 can also be readily reversed into a randomized or non-magnetic state by the application of a randomized magnetic field or electromagnetic disturbance of suitable strength, thereby erasing the fixed magnetic state. An example of a suitable magnetic layer is comprised of iron oxide embedded in a supporting polymer, approximately 0.2 inches in thickness.

A magnetic field can be applied by various means to form magnetized areas on layer 44. As illustrated in FIG. 5, a magnet 45, such as a permanent alloy magnet of pencil shape tapering to a 0.1 inch diameter, is moved across an exterior surface of top wall 43 to generate magnetized portions of magnetic layer 44 in the shape of identifying characters. As such, top wall 43 serves as a writing surface on which characters are formed, and the magnetized portions capture or hold imaging media 46. If magnetic layer 44 is coated or embedded in bottom wall 42, the magnetic writing would be applied on the interior surface of bottom wall 42.

If partition 20 is employed, partition 20 is positioned to its open position and container 40 is manipulated to effect flow of imaging media 46 from reservoir 18 across top wall 43. By causing the flow of imaging media 46 over top wall 43, a portion of imaging media 46 is captured and held by the magnetized areas in layer 44 of top wall 43. Container 40 can then be further manipulated to return the imaging media not collected by the magnetized portions back to reservoir 18. Partition 20 can then be positioned to its closed position, retaining the excess imaging media in reservoir 18. Thus, the magnetized portions of top wall 43 capture and hold imaging media 46 to allow the formation of an x-ray opaque image.

When the exposure to x-ray radiation is complete, handle 22 of partition 20 is rotated to position partition 20 in its open position. To de-magnetize the magnetized portions, a random magnetic field can be applied to top wall 43. Then, container 40 can be manipulated to effect flow of imaging media 46 into reservoir 18.

Imaging media 46 is comprised of a material opaque to x-ray radiation and attracted to a magnetic field. The permanent material characteristics of imaging media 46 are not altered by the magnetic field. Preferably, imaging media 46 is comprised of a plurality of generally spherical particles, either liquid or powder, which provide flow within recessed area 16 over top wall 43. The particles are preferably sized to optimize magnetic attraction to the magnetized portions, yet provide sufficient mass to flow across top wall 43. An example of a suitable material is a powder comprised of bismuth beads having a magnetically polarized coating. An additional coating can be applied to the bead to facilitate flow of the beads across top wall 43. The coating is selected to reduce static or physical absorption and minimize adhesion of the bismuth beads to the non-magnetized portions of top wall 43. A suitable imaging media 46 is comprised of approximately 30 percent fine lead powder, 50 percent iron oxide, and 20 percent polymer bonding material, each material having a roughly spherical shape and a diameter of about 0.02 inches to about 0.08 inches.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

Parts List 8 x-ray marker; first embodiment
10 container
12 bottom wall
14 side wall(s)
16 recessed area
18 reservoir
20 partition
22 handle
24 sheet
26 surface
28 writing implement
30 imaging media
32 cover
34 door; latch
36 opening
38 informational area
39 x-ray marker; second embodiment
40 container
42 bottom wall
43 top wall
44 magnetic layer
45 magnet
46 imaging media

What is claimed is:

1. A method for producing an x-ray marker for identifying radiation imaging recording media, comprising the steps of:

forming identifying characters on a marking area of a container transparent to radiation;

effecting flow of a particulate imaging media disposed in a reservoir within said container across said marking area, said imaging media being opaque to x-ray radiation;

capturing a portion of said particulate imaging media at said identifying characters; and effecting flow of said imaging media not captured at said identifying characters to said reservoir.

2. An x-ray marker apparatus for identifying radiation imaging recording media, comprising:

a container having a reservoir;

a sheet removably mounted within said container, said sheet having a deformable surface enabling a user to form depressions in said surface, said surface adapted to have depressions formed therein by a depression forming implement, said depressions cooperating to form identifying characters, said container and said sheet being transparent to x-ray radiation; and imaging media disposed in said reservoir comprised of material opaque to x-ray radiation, said imaging media comprised of a plurality of generally spherical particles adapted to flow from said reservoir across said surface through manipulation of said container, a portion of said particles being collected in said depressions.

3. An apparatus for identifying radiation imaging recording media, comprising:

a container having a recessed area and a reservoir communicable with said recessed area;

a surface disposed within said recessed area, said surface including a marking area on which identifying characters are formed using a marking instrument, said container and said surface being transparent to radiation, said surface being a magnetic surface adapted to be magnetized by a magnetic field applied to said container to form magnetized areas in said marking area, and said imaging media being attracted to said magnetized areas; and imaging media disposed within said reservoir comprised of material opaque to radiation, said imaging media comprised of a plurality of generally spherical particles adapted to flow from said reservoir into said recessed area and across said surface, a portion of said particles being collected at said identifying characters.

4. A method for producing an x-ray marker for identifying radiation imaging recording media, comprising the steps of:

forming depressions in a deformable surface of a sheet, said depressions cooperating to form identifying characters;

removably mounting said sheet in a container, said container and said sheet being transparent to x-ray radiation;

effecting flow of an imaging media disposed in a reservoir within said container across said deformable surface, said imaging media comprised of generally spherical particles and being opaque to x-ray radiation;

collecting a portion of said imaging media in said depressions; and effecting flow of said imaging media not collected in said depressions to said reservoir.

5. The method according to claim 4 wherein flow of said imaging media is effected by manipulating said container.

6. The method according to claim 4 further comprising the step of manipulating said container to effect flow of said portion of imaging media collected within said depressions to said reservoir, thereby collecting said imaging media within said reservoir.

7. The method according to claim 4 further comprising the step of removing said deformable surface from said container.

8. A method for producing an x-ray marker for identifying radiation imaging recording media, comprising the steps of:

applying a magnetic field to a magnetic surface of a container, said surface and said container being transparent to x-ray radiation;

forming magnetized areas on said magnetic surface, said magnetized areas cooperating to form identifying characters;

effecting flow of an imaging media disposed in a reservoir within said container across said surface, said imaging media comprised of generally spherical particles and being opaque to x-ray radiation, said imaging media being attracted to a magnetic field;

collecting a portion of said imaging media at said magnetized areas; and effecting flow of said imaging media not collected at said magnetized areas to said reservoir.

9. The method according to claim 8 wherein flow of said imaging media is effected by manipulating said container.

10. An apparatus for identifying radiation imaging recording media, comprising:

a container having a recessed area and a reservoir communicable with said recessed area;

a surface disposed within said recessed area, said surface including a marking area on which identifying characters are formed using a marking instrument, said container and said surface being transparent to radiation; and imaging media disposed within said reservoir comprised of material opaque to radiation, said imaging media comprised of a plurality of particles adapted to flow from said reservoir into said recessed area and across said surface, a portion of said particles being collected at said identifying characters.

11. An apparatus for identifying radiation imaging recording media, comprising:

a container having a recessed area and a reservoir communicable with said recessed area;

a surface disposed within said recessed area, said surface including a marking area on which identifying characters are formed using a marking instrument, said container and said surface being transparent to radiation, said marking area of said surface being deformable to form depressions, said depressions cooperating to form said identifying characters; and imaging media disposed within said reservoir comprised of material opaque to radiation, said imaging media comprised of a plurality of generally spherical particles adapted to flow from said reservoir into said recessed area and across said surface, a portion of said particles being collected at said identifying characters.

12. A method for producing an x-ray marker for identifying radiation imaging recording media, comprising the steps of:

forming identifying characters on a marking area of a container transparent to radiation by applying a magnetic field to a magnetic surface of a container to form magnetized areas on said magnetic surface, said magnetized areas cooperating to form said identifying characters;

effecting flow of an imaging media disposed in a reservoir within said container across said marking area, said imaging media comprised of generally spherical particles and being opaque to x-ray radiation;

collecting a portion of said imaging media at said identifying characters; and effecting flow of said imaging media not collected at said identifying characters to said reservoir.

13. An x-ray marker apparatus for identifying radiation imaging recording media, comprising:

a container having a reservoir;

a sheet removably mounted within said container, said sheet having a deformable surface enabling a user to form depressions in said surface by means of compression of said surface, said depressions cooperating to form identifying characters, said container and said sheet being transparent to x-ray radiation; and imaging media disposed in said reservoir comprised of material opaque to x-ray radiation, said imaging media comprised of a plurality of generally spherical particles adapted to flow from said reservoir across said surface through manipulation of said container, a portion of said particles being collected in said depressions.

14. The apparatus according to claim 13 further comprising movable means for securing said imaging media within said reservoir.

15. The apparatus according to claim 13 wherein said container includes a cover, sidewalls, and a bottom wall defining an enclosed area, said container having an opening through which to insert said sheet into said enclosed area.

16. The apparatus according to claim 13 wherein said container includes a recessed area communicable with said reservoir, said sheet disposed within said recessed area, the portion of said imaging media not collected in said depressions being collected in said reservoir through further manipulation of said container wherein said imaging media flows from said recessed area to said reservoir.

17. The apparatus according to claim 13 wherein said depressions have a width w and said imaging media has a diameter of approximately w/20.

18. The apparatus according to claim 13 wherein said imaging media has a diameter from about 0.005 inches to about 0.2 inches.

19. The apparatus according to claim 13 wherein said imaging media is a powder comprised of bismuth or copper-coated lead having a diameter of about 0.015 inches.

20. An x-ray marker apparatus for identifying radiation imaging recording media, comprising:

a container having a reservoir;

a magnetic surface mounted within said container communicable with said reservoir, said surface adapted to be magnetized by a magnetic field applied to said container by magnetization means to form magnetized areas on said surface, said container and said surface being transparent to x-ray radiation; and imaging media disposed within said reservoir comprised of material opaque to x-ray radiation and attracted to a magnetic field, said imaging media comprised of a plurality of generally spherical particles adapted to flow across said surface through manipulation of said container, a portion of said particles being collected at said magnetized areas.

21. The apparatus according to claim 20 further comprising movable means for securing said imaging media within said reservoir.

22. The apparatus according to claim 20 wherein said container includes a cover, sidewalls, and a bottom wall defining an enclosed area.

23. The apparatus according to claim 20 wherein said container includes a recessed area communicable with said reservoir, the portion of said imaging media not collected at said magnetized areas being collected in said reservoir through further manipulation of said container wherein said imaging media flows from said recessed area to said reservoir.

24. The apparatus according to claim 20 wherein said imaging media is comprised of bismuth having a magnetically polarized coating.

25. The apparatus according to claim 20 wherein said imaging media is comprised of approximately 30 percent fine lead powder, 50 percent iron oxide, and 20 percent polymer bonding material, each material having a diameter of about 0.02 inches to about 0.08 inches.

26. A method for producing an x-ray marker for identifying radiation imaging recording media, comprising the steps of:

forming identifying characters on a marking area of a container transparent to radiation by forming depressions in a deformable surface of a sheet, said depressions cooperating to form said identifying characters;

effecting flow of an imaging media disposed in a reservoir within said container across said marking area, said imaging media comprised of generally spherical particles and being opaque to x-ray radiation;

collecting a portion of said imaging media at said identifying characters; and effecting flow of said imaging media not collected at said identifying characters to said reservoir.

* * * * *